United States Patent [19]

Shirai et al.

[11] Patent Number: 5,082,669
[45] Date of Patent: Jan. 21, 1992

[54] RAPID-RELEASING ORAL PARTICLE PHARMACEUTICAL PREPARATION WITH UNPLEASANT TASTE MASKED

[75] Inventors: Yoshimi Shirai, Ikeda; Kiyomi Sogo, Osaka; Yoshihiko Nakamura, Takarazuka; Hiroshi Fujioka, Ibaraki; Hirokazu Makita, Nara, all of Japan

[73] Assignee: Dainippon Pharmaceutical Co., Ltd., Osaka, Japan

[21] Appl. No.: 553,960

[22] Filed: Jul. 18, 1990

[30] Foreign Application Priority Data

Jul. 20, 1989 [JP] Japan .................................. 1-190009

[51] Int. Cl.$^5$ ................................................. A61K 9/14
[52] U.S. Cl. ...................................... 424/495; 424/461; 424/462; 424/470; 424/480; 424/482; 424/494; 424/497
[58] Field of Search ............... 424/494, 495, 480, 461, 424/462, 470, 482, 497

[56] References Cited

U.S. PATENT DOCUMENTS 4,462,982  7/1984  Samejima et al. ................. 424/495
4,871,549 10/1989  Ueda et al. ......................... 424/494

FOREIGN PATENT DOCUMENTS 0277042  6/1988  European Pat. Off. .
2604044  9/1982  Fed. Rep. of Germany .
1272687  2/1962  France .
57-58631  4/1982  Japan .
63-258809 10/1988  Japan .
1059044  3/1965  United Kingdom .

Primary Examiner—Thurman K. Page
Assistant Examiner—Donald R. McPhail
Attorney, Agent, or Firm—Wenderoth, Lind & Ponack

[57] ABSTRACT

A rapid-releasing oral particle pharmaceutical preparation with its unpleasant taste masked comprising a core and a film layer coating the core, the core at least containing a drug having an unpleasant taste and a water-swelling agent, and the film layer at least containing ethylcellulose and a water-soluble substance, the amount of the drug in the core being at most 40% (based on the final particle preparation and so on), the amount of the water-swelling agent being about 35% to about 70%, the amount of ethylcellulose in the film layer being about 3 to about 11%, and the amount of the water-soluble substance being about 0.1 to about 0.8 times the weight of the ethylcellulose.

22 Claims, No Drawings

RAPID-RELEASING ORAL PARTICLE PHARMACEUTICAL PREPARATION WITH UNPLEASANT TASTE MASKED

FIELD OF THE INVENTION

This invention relates to a rapid-releasing oral particle pharmaceutical preparation with an unpleasant taste masked. More specifically, it relates to a particle pharmaceutical preparation which can be orally administered without a sensation of an unpleasant taste of the drug and which is rapidly released in the stomach.

DESCRIPTION OF THE PRIOR ART

As pharmaceutical preparations in which the unpleasant taste of a drug is masked, matrix preparations in which a drug is dispersed in a matrix component and coated preparations in which a drug is coated with a film are mainly known.

Generally, in the matrix preparations, a part of the drug is exposed on the surface of the preparations, and therefore, when the drug has a very strong unpleasant taste, the effect cannot be obtained of masking the unpleasant taste. In the case of the coated preparations, the effect of masking a unpleasant taste is excellent, but usually, it is not rapid-releasing.

Pharmaceutical preparations for the purpose of masking an unpleasant taste and effecting rapid release include fine particles obtained by coating nuclear particles with a water-soluble coating agent and then with a saliva-insoluble (i.e. enteric juice-soluble coating agent) such as carboxymethylethylcellulose Japanese Laid-Open Patent Publication No. 258809/1988 (an abstract of which is disclosed in Central Patents Index published by Derwent Publications Ltd., under Accession No. (hereinafter abbreviated as Der. No.) 88-348774/49)) and an oral corrigent preparations coated with a gastric juice-soluble polymeric substance such as polyvinyl acetal diethylaminoacetate (EP Patent Publication No. 277042A; Der. No. 88-214423/31). It is known, however, that the solubility of such an enteric juice-soluble or gastric juice-soluble film is dependent on pH, and it is known that the release of the drug varies with the variations in the pH of the gastric juice.

Pharmaceutical preparations coated with film-forming water-insoluble polymers such as ethylcellulose which do not vary in solubility depending upon the variations in pH were have been developed.

For example, U.S. Pat. No. 4,871,549 (Der. No. 87-30779/05) discloses a time-controlled explosion system (i.e., TCES) obtained by coating a core containing a drug and a water-swelling agent with ethylcellulose. The TCES is adapted to control the "lag times" by varying the thickness of the ethylcellulose layer. This TCES is not a rapid releasing preparation, but is a sustained releasing preparation. Furthermore, the purpose of this TCES is not to mask an unpleasant taste. When the ethylcellulose layer on the TCES is thin, the lag times will be short but an unpleasant taste cannot be masked. This is shown in Comparative Examples 6 to 8 given hereinafter. Furthermore, if the thicknesses of the ethylcellulose layers in the individual particles are not uniform, the lag times cannot be considered to be controlled. To form ethylcellulose layers of uniform thickness, the core should be of a shape near a sphere, and be free from strains, and have a particle diameter which is large to some extent. Incidentally, the TCES has Nonpareil seed (Freund Industrial Co., Ltd.) as the center of a core, and the TCES itself is said to have a particle diameter of 0.5 to 20 mm. In this way, TCES has a relatively large minimum particle diameter, and its shape is limitative.

Furthermore, Japanese Laid-Open Patent Publication No. 58631/1962 (Der. No. 40147E/20) discloses a granular composition coating with ethylcellulose and water-soluble polymer in which the bitter taste of the drug is masked, and the drug is rapidly released. In this patent, the drug to be contained in granules is limited to one of which disagreeable taste is of a weak degree. It is unsuitable for including a drug having a strong unpleasant taste, because it cannot mask an unpleasant taste, or if the coating is performed to a thickness sufficient to mask the unpleasant taste, the release of the drug from the granules is retarded. This is shown in Comparative Examples 1 and 2 shown hereinbelow.

PROBLEMS SOUGHT TO BE SOLVED BY THE INVENTION

It is a first object of this invention to provide a particle pharmaceutical preparation comprising a specific proportion of specific pharmaceutical components containing a drug having an unpleasant taste which can be administered without a sensation of the unpleasant taste.

It is a second object of this invention to provide a particle pharmaceutical preparation in which the drug is rapidly released in the stomach from the orally administered preparation.

Still another object of this invention is to provide a rapid-releasing pharmaceutical preparation in the form of small particles or granules in which the unpleasant taste of the drug is masked.

A further object of this invention is to provide a process for preparing the said particle phamaceutical preparation.

Other objects of this invention will become more apparent from the following detailed description.

MEANS FOR SOLVING THE PROBLEMS

Investigations of the present inventors led to the discovery that the above objects and advantages are achieved by a rapid-releasing oral particle pharmaceutical preparation with its unpleasant taste masked comprising a core and a film layer coating the core, the core at least containing a drug having an unpleasant taste and a water-swelling agent, and the film layer at least containing ethylcellulose and a water-soluble substance, the amount of the drug in the core being at most 40 % (% by weight based on the final particle preparation; hereinafter all percentages are on the same basis), the amount of the water-swelling agent being about 35 % to about 70 %, the amount of ethylcellulose in the film layer being in an amount of about 3 to about 11 % and the amount of the water-soluble substance being about 0.1 to about 0.8 times the weight of ethylcellulose.

The present invention is directed to a relatively small particle preparation in the form of powders or granules. When it is orally administered, persons who have taken it do not at all, or hardly sense an unpleasant taste. Moreover when this preparation reaches the stomach, the drug is released rapidly from the preparation to achieve its pharmacological effect. To the best of the knowledge of the present inventors, there has been known no particle pharmaceutical preparation which is rapid-releasing without a sensation of the strong unpleasant taste of the drug.

The particle pharmaceutical preparation of this invention will be described in detail hereinbelow.

The preparation of this invention is formed from a core and a film layer coating the core. The core at least contains a drug having an unpleasant taste and a water-swelling agent, and may further contain other components. The "unpleasant taste" is such that when the drug is directly administered orally, most persons feel unpleasant tastes such as bitterness, an astringent taste, and an irritating taste. The present invention can, however, be applicable to any drugs irrespective of the degree or type of the unpleasant taste.

The drugs to be applicable to this invention include pyridonecarboxylic acid antibacterial agents whose degree of unpleasantness is said to be strongest, such as 5-amino-1-cyclopropyl-6,8-difluoro-7-(cis-3,5-dimethyl-1-piperazinyl)-1,4-dihydro-4-(oxoquinoline-3-carboxylic acid, Enoxacin, Pipemidic acid, Ciprofloxacin, Ofloxacin, and Pefloxacin; antiepileptic drugs such as Zonisamide; macrolide antibiotics such as Erythromycin; beta-lactam antibiotics such as penicillins or cephalosporins; psychotropic drugs such as Chlorpromazine; cardiotonics such as Digitoxin; analgesic-antipyretic drugs such as Sulpyrine; and antiulcer drugs such as Cimetidine. Suitable among these drugs are pyridonecarboxylic acid antibacterial agents, especially 5-amino-1-cyclopropyl-6,8-difluoro-7-(cis-3,5-dimethyl-1-piperazinyl)-1,4-dihydro-4-oxoquinoline-3-carboxylic acid or Enoxacin, because the preparations of this invention have an excellent effect of masking the unpleasant taste.

The proportion of the drug having an unpleasant taste is not more than 40 % by weight based on the final preparation. Unless otherwise specified, all percents mean the weight percents based on the final preparation (the same hereinafter). The preferred proportion of the drug is about 5 to about 35 %, especially about 10 % to about 30 %.

The water-swelling agent used for the core in the preparation of this invention may be any substance which on contact with water swells in volume, preferably low substituted hydroxypropylcellulose, sodium carboxymethylstarch, carboxymethylcellulose or its salt, intercrosslinked carboxymethylcellulose, and polyvinylpolypyrrolidone, particularly, low substituted hydroxypropylcellulose is preferably used. The amount of water-swelling agent used is one which is sufficient to rupture the outer coating layer, and may vary depending upon the degree of the strength of its swelling function. The suitable amount is 35 to 70 %, preferably 40 to 60 %, especially preferably 45 to 55 %, based on the weight of the final preparation. If the amount of the water-swelling agent is smaller than 35 %, the rapid release of the drug from the preparation cannot be maintained. The water-swelling agent used in this invention has previously been known generally as a disintegrant. The amount of these substances as a disintegrant is usually 2 to 20 % based on the weight of the final preparation, and is far remote from that used in this invention.

Lactose and/or a binder may be further included to improve granularity and increase the yield of the preparation. The lactose and/or a binder is desirably used in an amount of about 3 to about 15 %, preferably about 4 to about 10 %. The binder may be any which is generally used, and preferred examples are hydroxypropylmethylcellulose, hydroxypropylcellulose and methylcellulose.

The core is produced by methods which are used to prepare ordinary fine granules. For example, all of the core components are charged into a high-speed mixer-granulator: Vertical Mixer-granulator (Powrex Corp.), and with stirring, ethanol and then, as required, water are added, and the mixture is kneaded. The kneaded mixture is then granulated and dried. Furthermore, the mixture may be sieved by a twin rotor, for example.

The core desirably has the drug, the water-swelling agent, and, as required, other components, uniformly mixed therein.

The content of the core in the final preparation of this invention is advantageously about 75 to about 95 %, preferably about 80 to about 93 %, most preferably about 85 to about 90 %. The shape of the core may be in the form of a true sphere or close to it or may be irregularly deformed. Its size is not particularly limited. As will be mentioned below, its size is automatically limited depending upon the size of the core preparation. For example, the core is preferably finished to powders having 5 % or less of particles with a size of at least 0.5 mm. It may be finished to granules having not more than 5 % of particles with a size of at least 1.4 mm.

In the particle preparation of this invention, the core is entirely coated with a film layer at least containing ethylcellulose and a water-soluble substance. The film layer may contain other pharmaceutical ingredients in addition to the two ingredients mentioned above.

In the film layer, the amount of ethylcellulose is generally about 3 to about 11 %, preferably about 4 to about 8 %, especially preferably about 4.2 to about 6 %. If the content of ethylcellulose is less than 3 %, the masking of an unpleasant taste is not performed sufficiently. On the other hand, if the content of ethylcellulose exceeds 11 %, the releasing of the drug from the final preparation is undesirably retarded. Ethylcellulose may be any of pharmaceutically acceptable ones, for example one in accordance with Japanese standards of pharmaceutical ingredients, namely one having an ethoxyl content of 46.5 to 51 % and having a viscosity of 7 to 100 cps in 5 % ethylcellulose/tolueneethanol solution (25° C.), specifically ETHOCEL grades of The Dow Chemical Co.

The water-soluble substance is another component which forms a film layer together with ethylcellulose. The water-soluble substance may be one which is soluble in water to some extent, preferabley a film-forming water-soluble polymer. Examples of such polymers include hydroxypropylmethylcellulose, hydroxypropylcellulose, methylcellulose, and polyvinylpyrrolidone. Of these, hydroxypropylmethylcellulose and hydroxypropylcellulose are preferred.

The proportion of the water-soluble substance to be used varies depending upon the proportion of ethylcellulose used. Generally, it i about 0.1 to about 0.8 times., preferably about 0.2 to about 0.7 times, especially preferably 0.3 timess to about 0.5 times, the weight of ethylcellulose.

The film layer may contain, in addition to ethyl cellulose and the water-soluble substance, other pharmaceutical components such as about 1 to about 5 % of titanium dioxide to prevent aggregation or adhesion of the final preparation itself, and about 0.5 to about 2 % of sucrose fatty acid ester for masking an unpleasant taste and the rapid release of the drug. The sucrose fatty acid esters are preferably those in which the fatty acid moiety is stearic acid.

The film layer is suitably formed from a blend of ethylcellulose and the water-soluble substance or a blend which further contains the other ingredients described above.

The content of the film layer is about 5 to about 25 %, preferably about 7 to about 20 %, most preferably about 10 to about 15 %.

The thickness of the film layer coating the core may be uniform or non-uniform, if the core is entirely coated. Generally, it is desirable to be uniform. Among the individual particles, the thickness of the film layer may be uniform or non-uniform. Desirably, it is uniform.

One important feature of this invention is that the preparation of this invention is particular, specifically that it is in the form of a powder or granular preparation. Preferably, it has an average particle diameter of not more than about 0.5 mm, more preferably about 0.1 to about 0.4 mm, especially preferably about 0.2 mm to about 0.3 mm. The average particle diameter denotes an average value of the diameters of the individual particles if it is assumed that they are true spheres.

Thus, when the particle preparation of this invention is orally administered, during the time when the preparation will stay in the mouth, the drug is sufficiently masked and gives off no unpleasant taste. Once the preparation is swallowed and reaches the stomach, the drug is rapidly released.

The particle preparation of this invention has a masking time, as measured by the method described below, of at least about 20 seconds, preferably about 20 to about 60 seconds. Furthermore, the particle preparation of this invention has a release rate, measured after 30 minutes by the method described below, of at least about 80 %, preferably about 83 to about 100 %.

The particle preparation of this invention may be prepared by making the core by the method described above, and coating it by a known method so as to form the film layer. For example, the coating may be carried out by coating the core with a solution or dispersion in a non-aqueous solvent containing components forming the film layer, namely at least containing ethylcellulose and a water-soluble substance. Suitable examples of the non-aqueous solvents are easily volatile organic solvents such as dichloromethane.

The coating of the core with the solution or dispersion is carried out by spraying the solution or dispersion by, for example, a coating apparatus, SPIR-A-FLOW (by Freund Industrial Co. Ltd.) and simultaneously removing the organic solvent.

When the resulting particle preparation contains a sucrose fatty acid ester in the film layer, it is heated at 60° to 75° C. for 10 to 20 hours. This results not only in preventing the aggregation and adhesion, but also in masking the unpleasant taste and in further improving the rapid release.

The resulting particle preparation of this invention masks an unpleasant taste of not only those drugs whose unpleasant taste is relatively weak such as Zonisamide, but also those having strong unpleasant taste such as pyridonecarboxylic acid antibacterial agents as an active ingredient. At the same time, the drugs can be rapidly released from the final product. The particle preparation of this invention does not give a separation of an unpleasant taste for at least about 20 seconds when one puts it into the mouth. Furthermore, in a dissolution test, at least 80 % of the drug is released within 30 minutes. The particle preparation of this invention which satisfies these conditions may be produced by properly selecting the amount of ethylcellulose which relates mainly to the masking of the unpleasant taste, the amounts of the water-swelling agent in the core which is considered to be involved in the release of the drug, and the amount of the water-soluble substance in the film layer from the ranges described hereinabove.

The following Examples and Comparative Examples illustrate the present invention in detail.

In the following Examples, the following drugs were used.

Drug A (Enoxacin: antibacterial agent)
1-ethyl-6-fluoro-1,4-dihydro-4-oxo-7-(1-piperazinyl)-1,8-naphthyridine-3-carboxylic acid.sesquihydrate Drug B (antibacterial agent)
5-amino-1-cyclopropyl-6,8-difluoro-7-(cis-3,5-dimethyl-1-piperazinyl)-1,4-dihydro-4-oxoquinoline-3-carboxllic acid Drug C (Zonisamide; antiepileptic drug)
1,2-benzisoxazole-3-methanesulfonamide Furthermore, in the following Examples and Comparative Examples, the following formulating components were used.

Ethylcellulose: ETHOCEL (10 cps) (The Dow Chemical Co.) in Example 15, ETHOCEL (100 cps)) was used.

L-HPC: low substituted hydroxypropylcellulose L-HPC LH31 of Shin-Etsu Chemical Co., Ltd. was used.

HPMC: hydroxypropylmethylcellulose (for a core component, TC-5R of Shin-etsu Chemical Co., Ltd. was used; for an outer coating layer, TC-5E of the same company was used.)

HPMCP: hydroxypropylmethylcellulose phthalate (HP-55 of Shin-etsu Checmial Co., Ltd. was used.)

SS Esters: sucrose stearate ester (RYOTO SUGAR ESTER S-770 of Mitsubishi-Kasei Foods Corp. was used.)

MC: methylcellulose (Metolose SM-15 of Shin-etsu Chemical Co., Ltd. was used.)

PVP: polyvinylpyrrolidone (PVP K30 of GAF Chemicals Corp. was used.)

PVPP: polyvinylpolypyrrolidone (Polyplasdone XL of GAF Chemicals Corp. was used.)

HPC: hydroxypropyl cellulose (for a core and a film layer, HPC-L of Nippon Soda Co., Ltd. were used.)

CMS-Na: sodium carboxymethylstarch (Primojel of AVEBE Veendam, Holland was used.)

CMC-Ca: calcium carboxymethylcellulose (ECG505 of Nichirin Chemical Industries Ltd. was used.)

Inter-crosslinked CMC: internally crosslinked sodium carboxymethylcellulose (Ac-Di-Sol of Asahi Chemical Industry Co., Ltd. was used.)

Titanium dioxide: TIPAQUE of Titanium Dioxide A-100 of Ishihara Sangyo Kaisha Ltd. wa used.

Lactose: lactose of B. V. Hollandsche Melksuikerfabrik was used.

In the following Examples and Comparative Examples, a powder preparation (having an average particle diameter of 0.2 to 0.3 mm) was prepared by the following methods.

PREPARATION FOR CORE COMPOSITION

All the core components were charged into a high-speed mixer-granulator: Vertical Mixer-granulator (Powrex Corp.), and mixed for 1 minute. 750 to 1200 ml of ethanol was added (when drug was other than drug B and HPMC was used as a binder, 210 to 450 ml of water was further added). The mixture was kneaded and granulated. The resultant was dried and sieved by a seiving machine (twin rotor) (screen: 32 mesh, produced by Hata Iron Works, Ltd.) to adjust the proportion of particles having a size of at least 0.5 mm to not more than 5 %.

COATING THE CORE COMPOSITION

All the film components were dispersed in dichloromethane so that its proportion became about 5 % by weight. 0.5 kg of a core composition was charged into a coating apparatus, SPIR-A-FLOW (Freund Industrial Co., Ltd.) and the coating suspension was sprayed, and dried. In Examples 21 and 23, the powder was further heated at 70° C. for 15 hours.

The resulting powder preparations were further subjected to the following dissolution test and organoleptic test.

SIMPLIFIED DISSOLUTION TEST (D 30 SEC.)

A powdery preparation corresponding to a drug amount of 50 mg was taken into a 10 ml by volume of an injection syringe, 10 ml of water was added, and over 30 seconds the injection syringe was reversed 10 times up and down. Thereafter, the powder suspension was filtered through a membrane filter (pore diameter of 0.45 $\mu$m), and the concentration of the drug (D 30 sec.) in the filtrate was measured. The threshold value (D 30 sec.; $\mu$/ml) was 25 $\mu$g/ml for drug A, 90 $\mu$g/ml for drug B, and 250 $\mu$/ml for drug C. In the following Examples and Comparative Examples, it was evaluated that unpleasant taste was masked when the D 30 sec. value was not more than 17 $\mu$g/ml for drug A, not more than 60 $\mu$g/ml for drug B, and not more than 200 $\mu$g/ml for drug C.

ORGANOLEPTIC TEST (Masking Time of the Unpleasant Taste)

When a particle preparation corresponding to 50 mg of the drug was put into the mouth, the masking time of the unpleasant taste was measured In the following Examples and Comparative Examples, the unpleasant taste was evaluated as having been masked when it was not sensed for at least about 20 seconds.

DISSOLUTION TEST (D 10 MIN., D 30 MIN.)

In accordance with the Paddle method described in The Pharmacopoeia of Japan, 11th edition (solvent: 900 ml of water dissolving 1.8 g of sodium chloride, the number of rotation: 50 rpm, temperature: 37° C., the amount of the preparation is corresponding to 50 mg of the drug) was carried out the dissolution test. When the dissolution rate (D 10 min.) after 10 minutes was at least 50 % and the dissolution rate after 30 minutes (D 30 min.) was at least 80 %, it was evaluated that the drug is rapid-releasing.

EXAMPLES 1-5

With regard to drug A or B, powder preparations were prepared with varying amounts of drug A or B and of water-swelling agents to obtain the results shown in the following table.

|  | Composition | Example 1 | 2 | 3 | 4 | 5 |
|---|---|---|---|---|---|---|
| Core components | Drug A (Enoxacin) | — | — | 20% | 10% | 5% |
|  | Drug B | 40% | 35% |  | — |  |
|  | L-HPC | 35% | 40% | 55% | 65% | 70% |
|  | Lactose |  | 8% |  | 6% |  |
|  | HPMC |  |  | 7% |  |  |
|  | (sub-total) |  | 90% |  | 88% |  |
| Film components | Ethylcellulose |  | 4.5% |  | 5.4% |  |
|  | HPMC |  | 2.2% |  | 2.7% |  |
|  | Titanium dioxide |  | 2.2% |  | 2.6% |  |
|  | SS ester |  | 1.1% |  | 1.3% |  |
|  | (sub-total) |  | 10% |  | 12% |  |
| Formulating characteristics | D 30 sec. (desired value: drug A → less than 17 $\mu$g/ml, drug B → less than 60 $\mu$g/ml) | 54 $\mu$g/ml | 52 $\mu$g/ml | 14 $\mu$g/ml | 10 $\mu$g/ml | 6 $\mu$g/ml |
|  | Masking time of an unpleasant taste (desired value: at least 20 sec.) | 21 sec. | 23 sec. | 25 sec. | 35 sec. | 42 sec. |
|  | D 10 min. (desired value: at least 50%) | 52% | 61% | 63% | 75% | 82% |
|  | D 30 min. (desired value: at least 80%) | 81% | 83% | 87% | 92% | 96% |

As shown in the above table, powder preparations having a drug content of 5 to 40 %, and a water-swelling agent content of 35 to 70 % had an unpleasant taste masked, and were rapid releasing.

EXAMPLES 6-10

With regard to drug A, powder preparations having varying amounts of ethylcellulose were prepared, and the results shown in the following table were obtained.

|  | Composition | Example 6 | 7 | 8 | 9 | 10 |
|---|---|---|---|---|---|---|
| Core components | Drug A (Enoxacin) |  |  | 20% |  |  |
|  | L-HPC |  |  | 52% |  | 50% |
|  | Lactose | 12.6% | 9.5% | 7.5% | 4% | 3% |

-continued

|  | Composition | Example 6 | 7 | 8 | 9 | 10 |
|---|---|---|---|---|---|---|
|  | HPMC |  |  | 7% |  | 5% |
|  | (sub-total) | 91.6% | 88.5% | 86.5% | 83% | 78% |
| Film components | Ethylcellulose | 4% | 5% | 6% | 8% | 10% |
|  | HPMC | 0.4% | 2.5% | 3.5% | 5% | 8% |
|  | Titanium dioxide |  |  | 2.7% |  |  |
|  | SS ester |  |  | 1.3% |  |  |
|  | (sub-total) | 8.4% | 11.5% | 13.5% | 17% | 22% |
| Formulating characteristics | D 30 sec. (desired value: less than 17 μg/ml) | 15 μg/ml | 15 μg/ml | 13 μg/ml | 15 μg/ml | 13 μg/ml |
|  | Masking time of an unpleasant taste (desired value: at least 20 sec.) | 22 sec. | 25 sec. | 27 sec. | 25 sec. | 27 sec. |
|  | D 10 min. (desired value: at least 50%) | 62% | 60% | 58% | 60% | 55% |
|  | D 30 min. (desired value: at least 80%) | 85% | 83% | 83% | 83% | 82% |

As shown in the above table, the powder preparations of Examples 6 to 10 which had an ethylcellulose content of 4 to 10 % and an HPMC content in the outer coating layer of 0.4 to 8 % were satisfactory in masking of an unpleasant taste and in rapid release.

EXAMPLES 11-14

Powder preparations were prepared using various water-swelling agents, and the results shown in the following table were obtained.

|  | Composition | Example 11 | 12 | 13 | 14 |
|---|---|---|---|---|---|
| Core components | Drug A (Enoxacin) |  |  | 20% |  |
|  | L-HPC | 52% |  |  |  |
|  | CMS-NA |  | 52% |  |  |
|  | CMC-Ca |  |  | 52% |  |
|  | Crosslinked CMC |  |  |  | 52% |
|  | Lactose |  |  | 9% |  |
|  | HPMC |  |  | 7% |  |
|  | (sub-total) |  |  | 88% |  |
| Film components | Ethylcellulose |  |  | 5.4% |  |
|  | HPMC |  |  | 2.7% |  |
|  | Titanium dioxide |  |  | 2.6% |  |
|  | SS ester |  |  | 1.3% |  |
|  | (sub-total) |  |  | 12% |  |
| Formulating characteristics | D 30 sec. (desired value: less than 17 μg/ml) | 14 μg/ml | 16 μg/ml | 16 μg/ml | 13 μg/ml |
|  | Masking time of an unpleasant taste (desired value: at least 20 sec.) | 25 sec. | 22 sec. | 22 sec. | 25 sec. |
|  | D 10 min. (desired value: at least 50%) | 58% | 54% | 52% | 52% |
|  | D 30 min. desired value at least 80%) | 82% | 87% | 82% | 82% |

As shown in the above table, by using any of these water-swelling agents (i.e., L-HPC, CMS-Na, CMC-Ca and inter-crosslinked CMC), powder preparations having desirable pharmaceutical preparative properties could be obtained. When the same amount of PVPP was used as the water-swelling agent, the same degree of results were obtained.

EXAMPLES 15-20

Powder preparations were prepared using various water-soluble substances, and the results shown in the following table were obtained.

|  | Composition | Example 15 | 16 | 17 | 18 | 19 | 20 |
|---|---|---|---|---|---|---|---|
| Core components | Drug B |  |  |  | 20% |  | — |
|  | Drug C (Zonisamide) |  |  |  | — |  | 20% |
|  | L-HPC |  |  |  | 52% |  |  |
|  | Lactose |  |  |  | 13% |  |  |
|  | HPC |  |  |  | 5% |  |  |
|  | (sub-total) |  |  |  | 90% |  |  |
| Film components | Ethylcellulose | 4.5%* |  |  | 4.5% |  | 2.2% |
|  | HPMC |  | 2.2% |  |  |  | 2.2% |
|  | MC |  |  | 2.2% |  |  | — |
|  | HPC |  |  |  | 2.2% |  | — |
|  | PVP |  |  |  |  | 2.2% | — |
|  | Titanium dioxide |  |  |  | 2.2% |  |  |
|  | SS ester |  |  |  | 1.1% |  |  |
|  | (sub-total) |  |  |  | 10% |  |  |
| Formulating characteristics | D 30 sec. (desired value: drug B → less than 60 μg/ml, drug C → less than 200 μg/ml) | 39 μg/ml | 42 μg/ml | 45 μg/ml | 40 μg/ml | 50 μg/ml | 60 μg/ml |

-continued

| Composition | Example | | | | | |
|---|---|---|---|---|---|---|
| | 15 | 16 | 17 | 18 | 19 | 20 |
| Masking time of an unpleasant taste (desired value: at least 20 sec.) | 33 sec. | 30 sec. | 30 sec. | 33 sec. | 25 sec. | 57 sec. |
| D 10 min. (desired value: at least 50%) | 69% | 74% | 76% | 70% | 76% | 63% |
| D 30 min. (desired value: at least 80%) | 81% | 83% | 85% | 81% | 88% | 82% |

*In Example 15 alone, ethylcellulose having a viscosity of 100 cps was used.

As shown in the above table, desirable powder preparations were obtained by using any of water-soluble substances (i.e., HPMC, MC, HPC, or PVP) were obtained.

EXAMPLES 21-24

Powder preparations shown in the following table were prepared to determine what powder preparation would result when lactose or sucrose fatty acid ester (SS ester) was present or absent, and when the final heating step was performed or not performed if the sucrose fatty acid ester (SS ester) was present. The following table also shows the results of Example 16 for comparison.

| | Composition | Example | | | | |
|---|---|---|---|---|---|---|
| | | 16 | 21 | 22 | 23 | 24 |
| Core components | Drug B | | | 20% | | |
| | L-HPC | | 52% | | | 62% |
| | Lactose | | 13% | | | — |
| | HPC | | 5% | | | 8% |
| | (sub-total) | | | 90% | | |
| Film components | Ethylcellulose | | | 4.5% | | |
| | HPMC | | | 2.2% | | |
| | Titanium dioxide | 2.2% | 3.3% | | 2.2% | 3.3% |
| | SS ester | 1.1% | — | | 1.1% | — |
| | (sub-total) | | | 10% | | |
| Heat treatment at 70° C. for 15 hours | | No | Yes | No | Yes | No |
| Formulating characteristics | D 30 sec. (desired value: less than 60 μg/ml) | 42 μg/ml | 33 μg/ml | 48 μg/ml | 38 μg/ml | 53 μg/ml |
| | Masking time of an unpleasant taste (desired value: at least 20 sec.) | 30 sec. | 40 sec. | 25 sec. | 38 sec. | 23 sec. |
| | D 10 min. (desired value: at least 50%) | 74% | 80% | 70% | 80% | 72% |
| | D 30 min. (desired value: at least 80%) | 83% | 95% | 80% | 95% | 83% |

As shown in the above table, any of the powder preparations showed satisfactory masking of an unpleasant taste and rapid release. The powder preparations of Examples 21 and 23 in which the heating step was performed in the presence of sucrose fatty acid ester (SS ester) showed the best masking effect of an unpleasant taste and the best rapid release.

COMPARATIVE EXAMPLES 1-4

The powder preparations for comparison shown in the following table were prepared, and their pharmaceutical preparative characteristics were examined.

| | Composition | Example 11 | Comparative Example | | | |
|---|---|---|---|---|---|---|
| | | | 1 | 2 | 3 | 4 |
| Core components | Drug A (Enoxacin) | | | 20% | | |
| | L-HPC | 52% | — | | 20% | |
| | Lactose | 9% | 61% | 53% | 41% | 37% |
| | HPMC | | | 7% | | |
| | (sub-total) | | 88% | 80% | 88% | 84% |
| Film components | Ethylcellulose | | | 5.4% | | 5.9% |
| | HPMC | | 2.7% | 9.0% | 2.7% | 5.9% |
| | Titanium dioxide | | 2.6% | 3.6% | 2.6% | 2.8% |
| | SS ester | | 1.3% | 2.0% | 1.3% | 1.4% |
| | (sub-total) | | 12% | 20% | 12% | 16% |
| Formulating characteristics | D 30 sec. (desired value: less than 17 μg/ml) | 14 μg/ml | 12 μg/ml | 52 μg/ml | 15 μg/ml | 50 μg/ml |
| | Masking time of an unpleasant taste (desired value: at least 20 sec.) | 25 sec. | 30 sec. | 8 sec. | 25 sec. | 12 sec. |
| | D 10 min. (desired value: at least 50%) | 58% | 5% | 18% | 5% | 13% |
| | D 30 min. (desired value: at least 80%) | 82% | 8% | 51% | 12% | 33% |

| | Example | Comparative Example | | | |
|---|---|---|---|---|---|
| Composition | 11 | 1 | 2 | 3 | 4 | value: at least 80%)

Comparative Examples 1 and 2 are common in that they do not contain L-HPC as a water-swelling agent and the ethylcellulose content is the same for both, and different in that in Comparative Example 1, the content of the water-soluble substance (HPMC) in the film layer is less than ⅛ of that in Comparative Example 2. The powder preparation of Comparative Example 1 which did not contain a water-swelling agent masked the strong unpleasant taste of drug A (Enoxacin) but lacked rapid release. The powder preparation of Comparative Example 2 in which the amount of the water-soluble substance in the film layer was increased over that in Comparative Example 1 had its release improved although to an unsatisfactory degree, but could not achieve masking of an unpleasant taste.

Comparative Examples 3 and 4 provided powder preparations in which the content of the water-swelling agent (L-HPC) in the core was only 20 %. In the powder preparation of Comparative Example 3, the unpleasant taste of drug A (Enoxacin) was nearly masked, but it lacked rapid releasing. With the powder preparation of Comparative Example 4 in which the content of the water-soluble substance increased from that in Comparative Example 3, release thereof was slightly improved, but the masking of the unpleasant taste was not effected.

COMPARATIVE EXAMPLES 5-8

The powder preparations for comparison shown in the following table were prepared, and their formulating characteristics (pharmaceutical preparative properties) were examined.

| | | Example | Comparative Example | | | |
|---|---|---|---|---|---|---|
| | Composition | 11 | 5 | 6 | 7 | 8 |
| Core components | Drug A (Enoxacin) | | | 20% | | |
| | L-HPC | | | 52% | | |
| | Lactose | | | 9% | | |
| | HPMC | | | 7% | | |
| | (sub-total) | | | 88% | | |
| Film components | Ethylcellulose | 5.4% | — | 1.3% | 2.7% | 5.5% |
| | HPMPC | — | 5.4% | | — | |
| | HPMC | 2.7% | | | | |
| | Titanium dioxide | 2.6% | 8.7% | 7.3% | 4.6% | |
| | SS ester | 1.3% | | 2.0% | | |
| | (sub-total) | | | 12% | | |
| Formulating characteristics | D 30 sec. (desired value: less than 17 μg/ml) | 14 μg/ml | 148 μg/ml | 102 μg/ml | 45 μg/ml | 7 μg/ml |
| | Masking time of an unpleasant taste (desired value: at least 20 sec.) | 25 sec. | 1 sec. | 3 sec. | 12 sec. | at least 30 sec. |
| | D 10 min. (desired value: at least 50%) | 58% | 95% | 70% | 48% | 13% |
| | D 30 min. (desired value: at least 80%) | 82% | 100% | 95% | 78% | 42% |

As shown in the above table, Comparative Example 5 is a powder preparation containing enteric coated HPMCP of an equal weight instead of ethylcellulose. This preparation is rapid releasing, but its unpleasant taste was not at all masked. The powder preparations of Comparative Examples 6 to 8 did not contain a water-soluble substance such as HPMC in the film layer. These powder preparations were rapid releasing when their ethylcellulose content was low, but the unpleasant taste of these preparations was not at all masked. On the other hand, as the ethylcellulose content increased, the unpleasant taste was masked but they become slow-releasing. Consequently, in the absence of a water-soluble substance, the content of ethylcellulose by which the unpleasant taste is masked and the preparation become rapid releasing is considered to be difficult to preset.

We claim:

1. A rapid-releasing oral particle pharmaceutical preparation comprising a plurality of particles, each of said particles comprising a core and a film layer coating said core, said core comprising a drug having a taste for which masking is desired and a water-swelling agent, said film layer comprising ethylcellulose and a water-soluble substance, said water-soluble substance being selected from the group consisting of hydroxypropylmethylcellulose, hydroxypropylcellulose, methylcellulose, and polyvinylpyrrolidone, the amount of said drug in said core being at most 40% by weight based upon the weight of said particle, the amount of said water-swelling agent being about 35% to about 70% by weight based upon the weight of said particle, the amount of ethylcellulose in said film layer being about 3 to about 11% by weight based upon the weight of said particle, the amount of said water-soluble substance being about 0.1 to about 0.8 times the weight of ethylcellulose, said core accounting for about 75-95% by weight of said particle, and wherein said preparation has the following properties:

(1) the length of time during which a preparation containing 50 mg of said drug kept in a mouth cannot be tasted is at least 20 seconds, (2) the dissolution rate of a preparation containing 50 mg of said drug is at least 50% after 10 minutes ($D_{10}min$) and at least 80% after 30 minutes ($D_{30}min$) according to the Paddle method.

2. The preparation according to claim 1 wherein the core has a drug dispersed in the water-swelling agent.

3. The preparation according to claim 1 in which the film layer is a blend of ethylcellulose and the water-soluble substance.

4. The preparation according to claim 1 in which the drug is contained in an amount of about 5 to about 35 %.

5. The preparation according to claim 1 in which the water-swelling agent is contained in an amount of about 40 to about 60 %.

6. The preparation according to claim 1 in which ethylcellulose is contained in an amount of about 4 to about 8 %.

7. The preparation according to claim 1 in which the water-soluble substance is contained in an amount of about 0.2 to about 0.7 times the weight of the ethylcellulose.

8. The preparation according to claim 1 which further contains lactose and/or a binder.

9. The preparation according to claim 8 in which lactose and/or a binder is contained in an amount of about 3 to about 15 %.

10. The preparation according to claim 1 in which the film layer further contains a sucrose fatty acid ester and/or titanium dioxide.

11. The preparation according to claim 10 which contains about 0.5 to about 2 % of the sucrose fatty acid ester, and/or about 1 to about 5 % of titanium dioxide.

12. The preparation according to claim 1 in which the content of the core is about 80 to about 93 %.

13. The preparation according to claim 1 in which the content of the film layer is about 5 to about 25 %.

14. The preparation according to claim 1 in which the content of the film layer is about 7 to about 20 %.

15. The preparation according to claim 1 which has an average particle diameter of not more than about 0.5 mm.

16. The preparation according to claim 1 which has an average particle diameter of about 0.1 mm to about 0.4 mm.

17. The preparation according to claim 1 in which the drug is an antibacterial agent, an antiepileptic agent, an antibiotic agent, a psychotropic agent, a cardioitonic, an antipyretic or an antiulcer agent.

18. The preparation according to claim 17 in which the antibacterial agent is a pyridonecarboxylic acid antibacterial agent.

19. The preparation according to claim 18 in which the pyridonecarboxylic acid antibacterial agent is 5-amino-1-cyclopropyl-6,8-difluoro-7-(cis-3,5-dimethyl-1-piperazinyl)-1,4-dihydro-4-oxoquinoline-3-carboxylic acid or Enoxacin.

20. The preparation according to claim 1 in which the water-swelling agent is low substituted hydroxypropylcellulose, sodium carboxymethylstarch, carboxymethylcellolose or its salt, inter-crosslinked carboxymethylcellulose or polyvinylpolypyrrolidone.

21. The preparation according to claim 1 in which the ethylcellulose has an ethoxyl content of about 46.5 to about 51 %.

22. A process for producing the rapid-releasing oral particle pharmaceutical preparation described in claim 1, which comprises coating a solution or a dispersion containing at least ethylcellulose and a water-soluble substance in a solvent on the surface of a core containing at least a drug having an unpleasant taste and a water-swelling agent, and then removing the solvent.

* * * * *